United States Patent
Blevis

(10) Patent No.: US 8,463,363 B2
(45) Date of Patent: Jun. 11, 2013

(54) SPECT IMAGE RECONSTRUCTION METHODS AND SYSTEMS

(75) Inventor: Ira Blevis, Zicron Yaakov (IL)

(73) Assignee: General Electric Company, Schenectady, NY (US)

(*) Notice: Subject to any disclaimer, the term of this patent is extended or adjusted under 35 U.S.C. 154(b) by 236 days.

(21) Appl. No.: 13/004,655

(22) Filed: Jan. 11, 2011

(65) Prior Publication Data

US 2012/0179021 A1 Jul. 12, 2012

(51) Int. Cl.
*A61B 6/00* (2006.01)
(52) U.S. Cl.
USPC .......................................... 600/436; 382/199
(58) Field of Classification Search
USPC .................. 382/199, 260; 348/222.1, 241
See application file for complete search history.

(56) References Cited

U.S. PATENT DOCUMENTS

| | | | |
|---|---|---|---|
| 7,242,002 B2 | 7/2007 | Blevis et al. | |
| 7,312,458 B2 | 12/2007 | Blevis | |
| 7,375,338 B1 | 5/2008 | Hugg et al. | |
| 7,495,225 B2 | 2/2009 | Hefetz et al. | |
| 2005/0205795 A1 | 9/2005 | Blevis et al. | |
| 2007/0263099 A1* | 11/2007 | Motta et al. | 348/222.1 |
| 2008/0151081 A1* | 6/2008 | Frank | 348/241 |
| 2008/0304619 A1 | 12/2008 | Blevis et al. | |
| 2010/0329418 A1 | 12/2010 | Blevis | |
| 2010/0329419 A1 | 12/2010 | Blevis | |

* cited by examiner

*Primary Examiner* — Unsu Jung
*Assistant Examiner* — Saurel J Selkin
(74) *Attorney, Agent, or Firm* — Fletcher Yoder, P.C.

(57) ABSTRACT

Image reconstruction techniques for a medical imaging system are provided that include receiving pixel data from a gamma camera of an imaging system, and calculating a subsequent voxel value from the pixel data by subtracting an expected pixel value from a measured pixel value of the pixel data to produce a difference and correcting a previous voxel value by adding a weighted value of the difference to the previous voxel value. An imaging system is also provided.

20 Claims, 11 Drawing Sheets

SPECT IMAGE RECONSTRUCTION METHODS AND SYSTEMS

BACKGROUND OF THE INVENTION

The subject matter disclosed herein relates to single photon emission computed tomography (SPECT), and more particularly to a technique for reconstruction of 3D source distributions in cardiac imaging using emission data.

A wide range of imaging techniques are known and currently in use, particularly for medical diagnostic applications. One such technique, SPECT, relies on the emission of gamma rays during the radioactive decay of a radioisotope (or radionuclide), commonly administered in the form of a radiopharmaceutical agent that can be carried, and in some cases, bound to particular tissues of interest. A SPECT scanner detects the emissions via a gamma camera that typically includes a collimator, a scintillator, and a series of photomultiplier tubes. The collimator allows only emissions in a particular direction to enter into the scintillator. The scintillator converts the gamma radiation into lower energy ultraviolet photons that impact regions (pixels) of the photomultiplier tubes. These, in turn, generate image data related to the quantity of radiation impacting the individual regions. Image reconstruction techniques, such as backprojection, may then be used to construct images of internal structures of the subject based upon this image data.

While such systems have proven extremely useful at providing high quality images with good diagnostic value, further refinement is needed. For example, SPECT imaging systems may use reconstruction techniques such as filtered backprojection or other techniques to reconstruct three-dimensional images. However such techniques, such as Maximum Likelihood Expectation Maximization (MLEM) or Block Sequential Regularized Expectation Maximization (BLREM), may not provide the desired performance and image quality and may be particularly sensitive to noise and the position of the subject.

BRIEF DESCRIPTION OF THE INVENTION

A method of reconstructing an image is provided. The method includes receiving pixel data from a gamma camera of an imaging system and calculating a voxel value from the pixel data. The calculation includes subtracting an expected pixel value from a measured pixel value of the pixel data to produce a difference and correcting a previous voxel value by adding a weighted value of the difference to the previous voxel value.

In another embodiment, an imaging system is provided. The imaging system includes a detector and image processing circuitry coupled to the module. The image processing circuitry executes code stored on a non-transitory, tangible machine-readable medium for reconstructing a three-dimensional image from pixel data received from the gamma camera, wherein the code, when executed, performs the following:
iteratively processes the pixel data to produce voxels of a three-dimensional image, wherein a voxel value $V_j^{(k+1)}$ of an iteration is determined such that:

$$V_j^{(k+1)} = V_j^{(k)} + \frac{1}{\sum m_{ij}^{-1}} \sum (P_i - \langle P_i \rangle) m_{ij}^{-1},$$

and where k is the iteration;
j is the voxel index
m is the geometrical weight;
P is the measured pixel value;
<P> is the expected/estimated pixel value; and
i is the pixel index.

Finally, another method of reconstructing an image is provided that includes detecting gamma radiation at a detector and iteratively processing pixel data received from the detector on processing circuitry of an image processing system to produce voxels of a three-dimensional image, wherein a voxel $V_j^{(k+1)}$ of an iteration is determined such that:

$$V_j^{(k+1)} = V_j^{(k)} + \frac{1}{\sum m_{ij}^{-1}} \sum (P_i - \langle P_i \rangle) m_{ij}^{-1},$$

and where
k is the iteration;
j is the voxel index
m is the geometrical weight;
P is the measured pixel value;
<P> is the expected/estimated pixel value; and
i is the pixel index.

BRIEF DESCRIPTION OF THE DRAWINGS

These and other features, aspects, and advantages of the present techniques will become better understood when the following detailed description is read with reference to the accompanying drawings in which like characters represent like parts throughout the drawings, wherein.

DETAILED DESCRIPTION OF THE INVENTION

Embodiments of the present techniques include an image reconstruction technique using an absolute error differences (AED) formula. The image reconstruction technique may include iteratively processing pixel data by determining the difference between error terms, e.g., the difference between a measured pixel value and an expected pixel value, and adding the error term difference to an iterative voxel value determination. Embodiments also include imaging systems implementing the image reconstruction technique.

Figure 1:
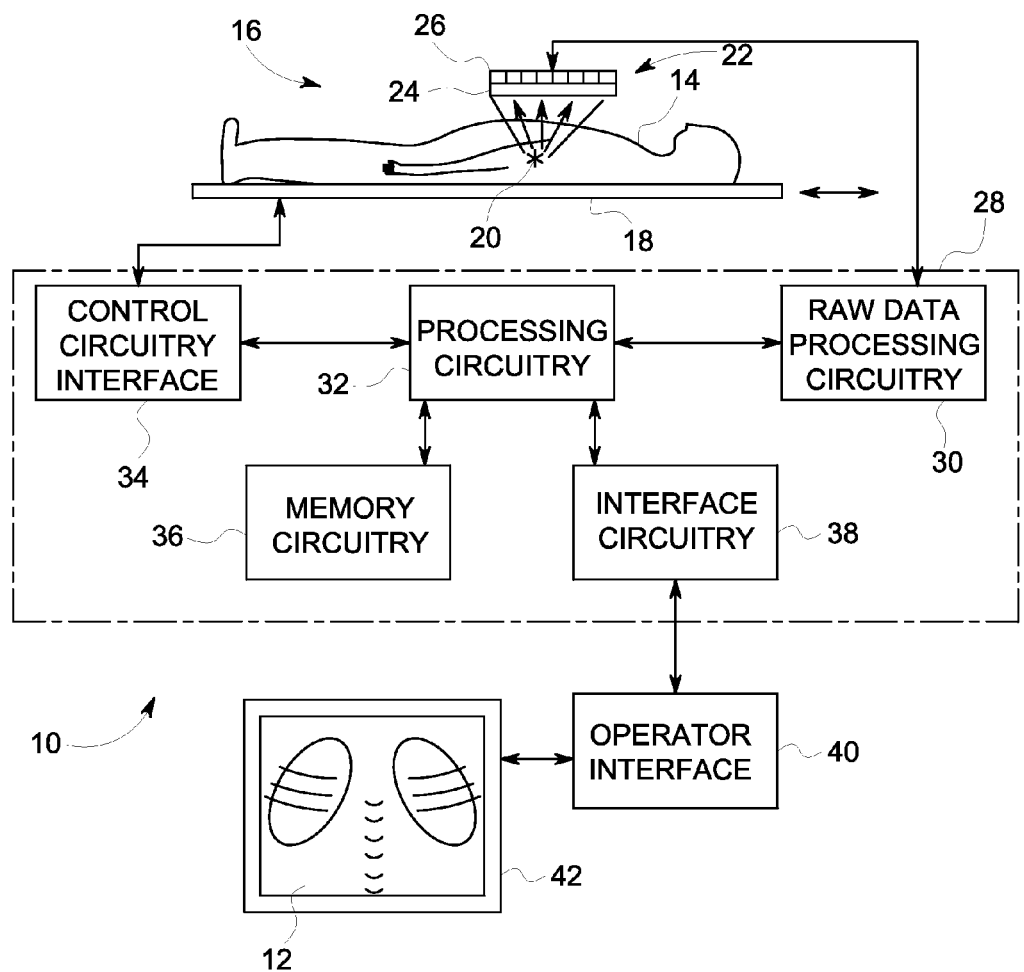
FIG. 1 is a diagrammatic representation of an exemplary SPECT imaging system incorporating aspects of the present techniques.

A diagrammatic representation of an exemplary SPECT imaging system is shown in FIG. 1. The system, designated generally by the reference numeral 10, is designed to produce useful images 12 of a subject 14. The subject is positioned in a scanner, designated by reference numeral 16 in which a patient support 18 is positioned. The support may be movable within the scanner to allow for imaging of different tissues or anatomies of interest within subject. Prior to image data collection, a radioisotope, such as a radiopharmaceutical substance (sometimes referred to as a radiotracer), is administered to the patient, and may be bound or taken up by particular tissues or organs. Typical radioisotopes include various radioactive forms of elements, although many in SPECT imaging are based upon an isotope of technetium ($^{99}$Tc) that emits gamma radiation during decay. Various additional substances may be selectively combined with such radioisotopes to target specific areas or tissues of the body. In some embodiments, the imaging system 10 may be an Ultrafast Dedicated Cardiac Camera (UFC) system.

Gamma radiation emitted by the radioisotope is detected by a digital detector or gamma camera 22. Although illustrated in the figure as a planar device positioned above the patient, in practice the camera may be positioned below the patient, both above and below the patient, and/or may wrap completely or partially around the patient. For example, the gamma cameras 22 may be arranged in one or more rings around the subject 16, such as 180° around the subject 16, 360° around the subject 16, etc. In general, the gamma camera 22 comprises one or more collimators and a scintillator or a solid state detector, together represented generally as reference numeral 24. In some embodiments, such as the UFC system mentioned above, the gamma camera 22 may include a cadmium zinc telluride (CZT) solid-state detector. The collimator allows gamma radiation emitted only in certain directions (typically perpendicular to the scintillator) to impact the scintillator. The scintillator, which is typically made of a crystalline material, such as sodium iodide (NaI), converts the received gamma radiation to lower energy light energy (e.g., in an ultraviolet range). Photomultiplier tubes 26 then receive this light and generate image data corresponding to photons impacting specific discrete picture element (pixel) regions. In other embodiments, the solid state detector converts the received gamma radiation into electrical signals. In some embodiments, the detector or gamma camera 22 may include one or more "modules." Each module may be a solid state detection module capable of detecting gamma radiation and producing data for an array of pixels. In some embodiments, a gamma camera may be referred to as including one or more detectors, and each detector may be referred to as including one or more modules.

The gamma camera 22 is coupled to system control and processing circuitry 28. This circuitry may include a number of physical and functional components that cooperate to allow the collection and processing of image data to create the desired images. For example, the circuitry may include raw data processing circuitry 28 that initially receives the data from the gamma camera 22, and that may perform various filtering, value adjustments, and so forth. Processing circuitry 32 allows for the overall control of the imaging system, and for manipulation of image data. The processing circuitry 32 may also perform calibration functions, correction functions, and so forth on the data. The processing circuitry 32 may also perform image reconstruction functions, such as based on certain algorithms (e.g., backprojection or iterative reconstruction). Such functions may also be performed in post-processing on local or remote equipment. The processing circuitry may interact with control circuitry/interface 34 that allows for control of the scanner and its components, including the patient support, camera, and so forth. Moreover, the processing circuitry 32 will be supported by various circuits, e.g., non-transitory tangible machine-readable media such as memory circuitry 36 that may be used to store image data, calibration or correction values, routines performed by the processing circuitry (e.g., as code stored on the memory circuitry 36), and so forth. Finally, the processing circuitry may interact with interface circuitry 38 designed to support an operator interface 40. The operator interface 40 allows for imaging sequences to be commanded, scanner and system settings to be viewed and adjusted, images to be viewed, and so forth. In the illustrated embodiment, the operator interface 40 includes a monitor 42 on which reconstructed images 12 may be viewed.

In certain implementations the processing circuitry 32 and 34 may include specially programmed hardware, memory, or processors (e.g., application-specific integrated circuits (ASICs)) for performing the AED image reconstruction as discussed below. Similarly, all or part of the image reconstruction may be performed using one or more general or special purpose processors and stored code or algorithms configured to execute on such processors. Likewise, a combination of special purpose hardware and/or circuitry may be used in conjunction with one or more processors configured to execute stored code to implement the steps discussed herein. The results of such data processing steps may be displayed on the monitor 42 of the operator interface 40.

In an institutional setting, the imaging system 10 may be coupled to one or more networks to allow for the transfer of system data to and from the imaging system, as well as to permit transmission and storage of image data and processed images. For example, a local area networks, wide area networks, wireless networks, and so forth may allow for storage of image data on radiology department information systems or on hospital information systems. Such network connections further allow for transmission of image data to remote post-processing systems, physician offices, and so forth.

Keeping in mind the SPECT imaging system 10 discussed above, or the corresponding components of other types of suitable imaging systems, a brief description of the functioning of one such system is provided to facilitate further explanation of the present approach. In particular, SPECT imaging is primarily used to measure metabolic activities that occur in tissues and organs and, in particular, to localize aberrant metabolic activity. In SPECT imaging, the patient is typically injected with a solution that contains a radioactive tracer. The solution is distributed and absorbed throughout by the body in different degrees, depending on the tracer employed and the functioning of the organs and tissues. In particular, the radioactive tracer emits positrons that interact with surrounding particles, thereby generating gamma rays or the tracer emits the gamma rays directly. In a SPECT imaging system 10, the gamma rays are detected by the gamma cameras 22. The gamma rays may be collimated so that the detection of a gamma ray may be used to determine the line of response along which the gamma ray traveled before impacting the detector, allowing localization of the emission source. By detecting a number of such gamma rays, and calculating the corresponding lines traveled by the gamma rays, the concentration of the radioactive tracer in different parts of the body may be estimated and a tumor, thereby, may be detected.

In view of these comments, and returning now to FIG. 1, the raw data processing circuitry 28 is adapted to read out signals generated in response to the gamma rays from the photomultiplier tubes 26 of the gamma cameras 22. The signals acquired by the raw data processing circuitry 28 are provided to the processing circuitry 32. The image reconstruction and processing circuitry generates an image based on the derived gamma ray emission locations. Each set of image data captured by one of and/or each position of the gamma cameras 22 may correspond to a 2-D projection made up of 2-D pixels. A reconstruction algorithm may be applied to the 2-D projections to reconstruct a 3-D image. As described below, such a reconstruction may be based on calculating voxels from pixel data. The operator interface 40 is utilized by a system operator to provide control instructions to some or all of the described components and for configuring the various operating parameters that aid in data acquisition and image generation. The monitor 42 may also display the generated image.

Figure 2:
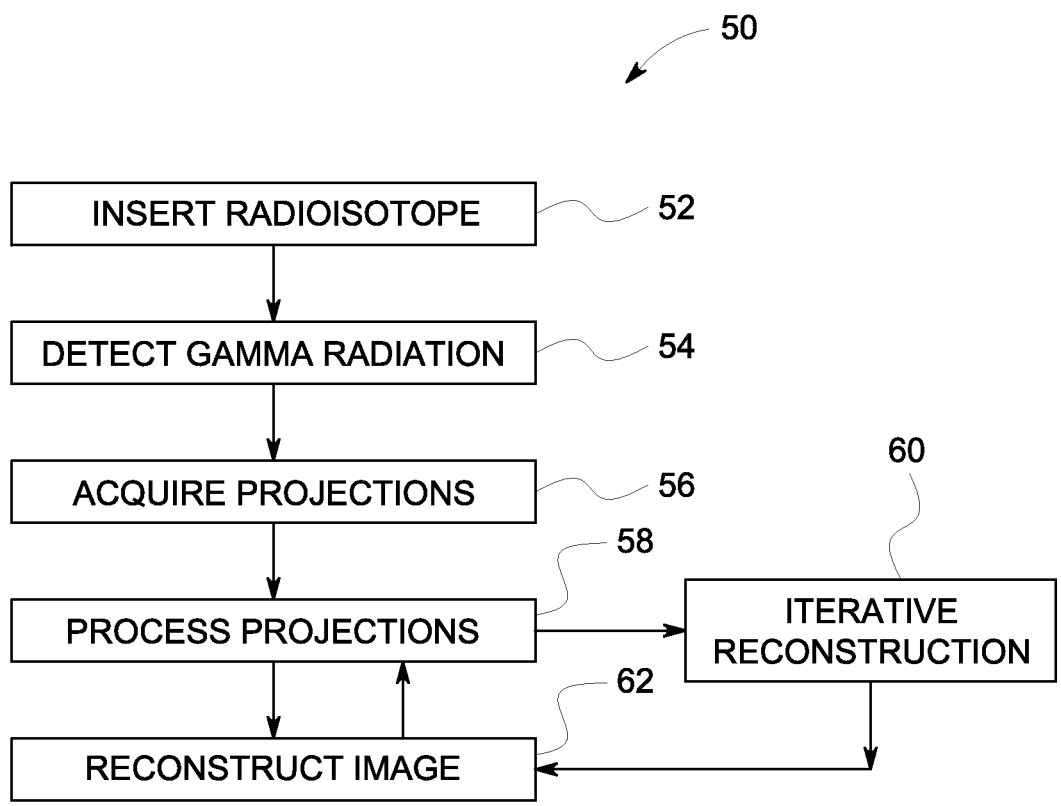
FIG. 2 is a flowchart of a process for acquiring and reconstructing a three-dimensional image in accordance with embodiments of the present techniques.

With the foregoing in mind, FIG. 2 depicts a process 50 for acquiring and reconstructing an image from the SPECT imaging system 10 in accordance with an embodiment of the present approach. Initially, a radioisotope may be inserted into the subject (block 52). After the desired physiological state is reached (for example, binding of the radioisotope within a particular organ of interest), the gamma radiation emitted from the radioisotope may be detected by the detectors or gamma cameras 22 (block 54). As noted above, this may include rotating one or more gamma cameras 22 around the subject or using a ring or subset of a ring of gamma cameras to detect gamma radiation around the subject.

As described above, projections may be acquired from the detected gamma radiation (block 56), such as from the photomultiplier tubes 26 and the raw data processing circuitry 28. The projections may be processed (block 58), such as by the processing circuitries 28 and 32. As described further below, such processing includes iterative reconstruction of the projection data using an AED formula (block 60). A three-dimensional image is reconstructed from the iterative processing of the projection data and, as seen below, may have enhanced features over standard reconstruction algorithms.

The iterative reconstruction described above uses an absolute error differences algorithm to perform the iterative reconstruction and calculate the voxels of the image. In the iterative reconstruction, the next voxel value is determined from a correction to the current voxel value. This process is repeated, i.e., iterated, until some completion criterion (e.g., a suitable degree of convergence, satisfaction of a cost function, a preset number of iterations, and so forth) is satisfied. In the AED formula discussed below, the correction is determined from the error term differences and the correction is added to the current voxel value. The AED formula may be expressed as:

$$V_j^{(k+1)} = V_j^{(k)} + \frac{1}{\sum m_{ij}^{-1}} \sum (P_i - \langle P_i \rangle) m_{ij}^{-1} \quad (1)$$

Wherein:
V is the voxel value;
k is the iteration;
j is the voxel index;
m is the geometrical weight;
P is the measured pixel value;
<P> is the expected/estimated pixel value; and
i is the pixel index.

As shown above, the correction is a weighted mean of the difference between measured pixel values and expected (estimated) pixel values. As shown below, the AED formula may provide for an emphasis on foreground pixels relative to background pixels of an image.

Figure 3:
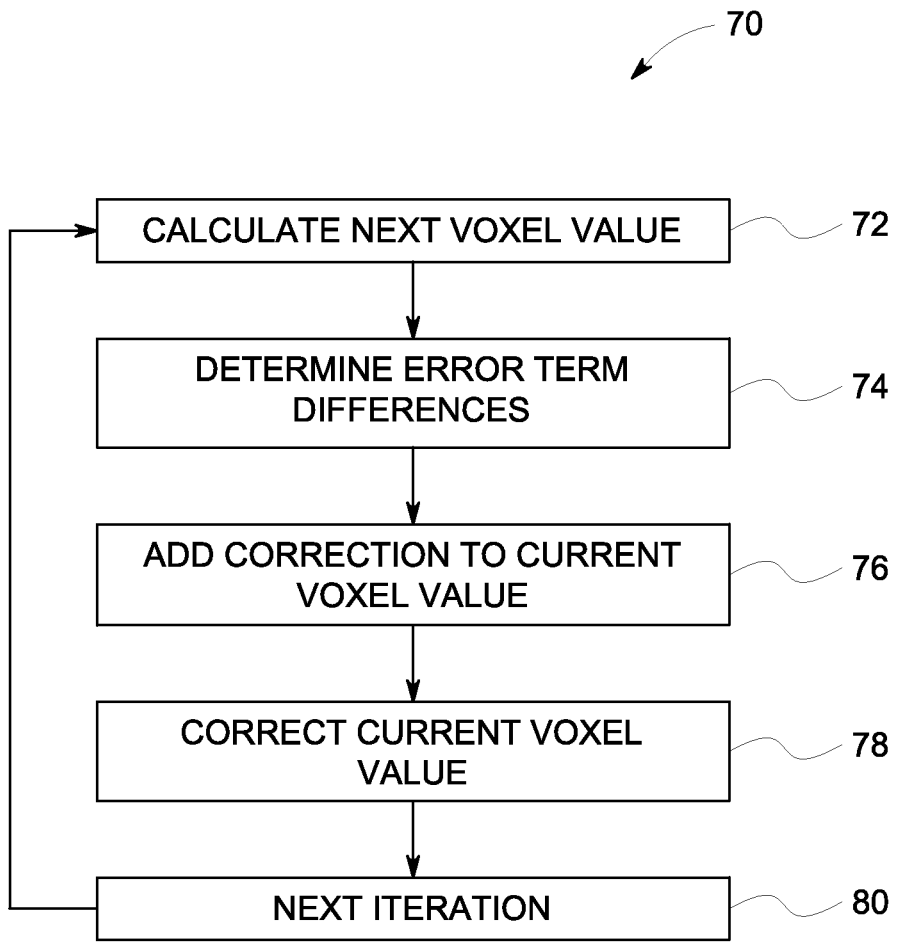
FIG. 3 is a flowchart of a process for iteratively calculating a voxel of a three-dimensional image in accordance with embodiments of the present techniques.

FIG. 3 depicts a process 70 for determining a voxel value using the AED formula (1) described above. As noted above, the process 70 may be implemented as code stored on a non-transitory tangible machine-readable medium, e.g., memory circuitry 36. As shown above, the voxel value of the (k+1)th iteration is calculated from the voxel value of the (k)th iteration according to formula (1) (block 72). The correction for the voxel is the sum of weighted differences between (block 74) the expected pixel values and the measured pixel values for the (k)th iteration, as shown above in formula (1). The weights $m_{ij}$ are determined from the geometrical overlap of the projection of the (i)th voxel onto the (j)th pixel. The weights are a function of the system geometrical design and can be calculated and stored in advance of the time of patient data acquisition and data reconstruction. This difference may be added to the previously calculated voxel value (voxel value (k)) (block 76) to correct the previous voxel value (block 78). After determining a voxel value based on this correction, the process may iterate to the next iteration (block 80).

Figure 4:
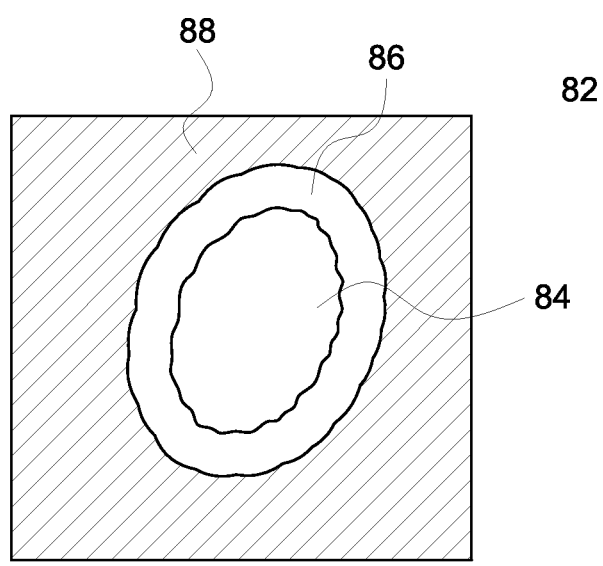
FIG. 4 depicts an image having a foreground and a background in accordance with embodiments of the present techniques.

FIG. 4 depicts a reconstructed image 82 of a region of interest 84 (e.g., an organ, lesion, or other anatomical structure or feature) of the subject in accordance with an embodiment of the present techniques. The image 82 may include a foreground 86 and a background 88. As seen in FIG. 4, the region of interest 82 may be primarily in the foreground 86 of the image. Thus, the AED formula discussed above may provide for emphasis of the foreground 86 relative to the background 88, in contrast to other techniques such as MLEM. For example, Table 1 depicts the voxel update factors for both the AED formula described above and an MLEM formula. The table depicts contributions to the voxel update factors calculated by each formula for a background pixel that has a measurement of 2 counts and a current estimate of 1 count and a foreground pixel that has a measurement of 100 counts and current estimation of 80 counts:

TABLE 1

Comparison of AED and MLEM voxel update factors

| | | |
|---|---|---|
| Background | Measured | 2 |
| Background | Projected | 1 |
| Background | MLEM | 2 |
| Background | AED | 1 |
| Foreground | Measured | 100 |
| Foreground | Projected | 80 |
| Foreground | MLEM | 1.2 |
| Foreground | AED | 20 |

As shown above, the MLEM voxel calculation is dominated by the 2 of the background over the 1.2 of the foreground. In contrast, the AED voxel calculation is dominated by the 20 of the foreground over the 1 of the background. Accordingly, in certain embodiments, the AED formula may provide increased emphasis of the foreground of a reconstructed image relative to the background.

Figure 5:
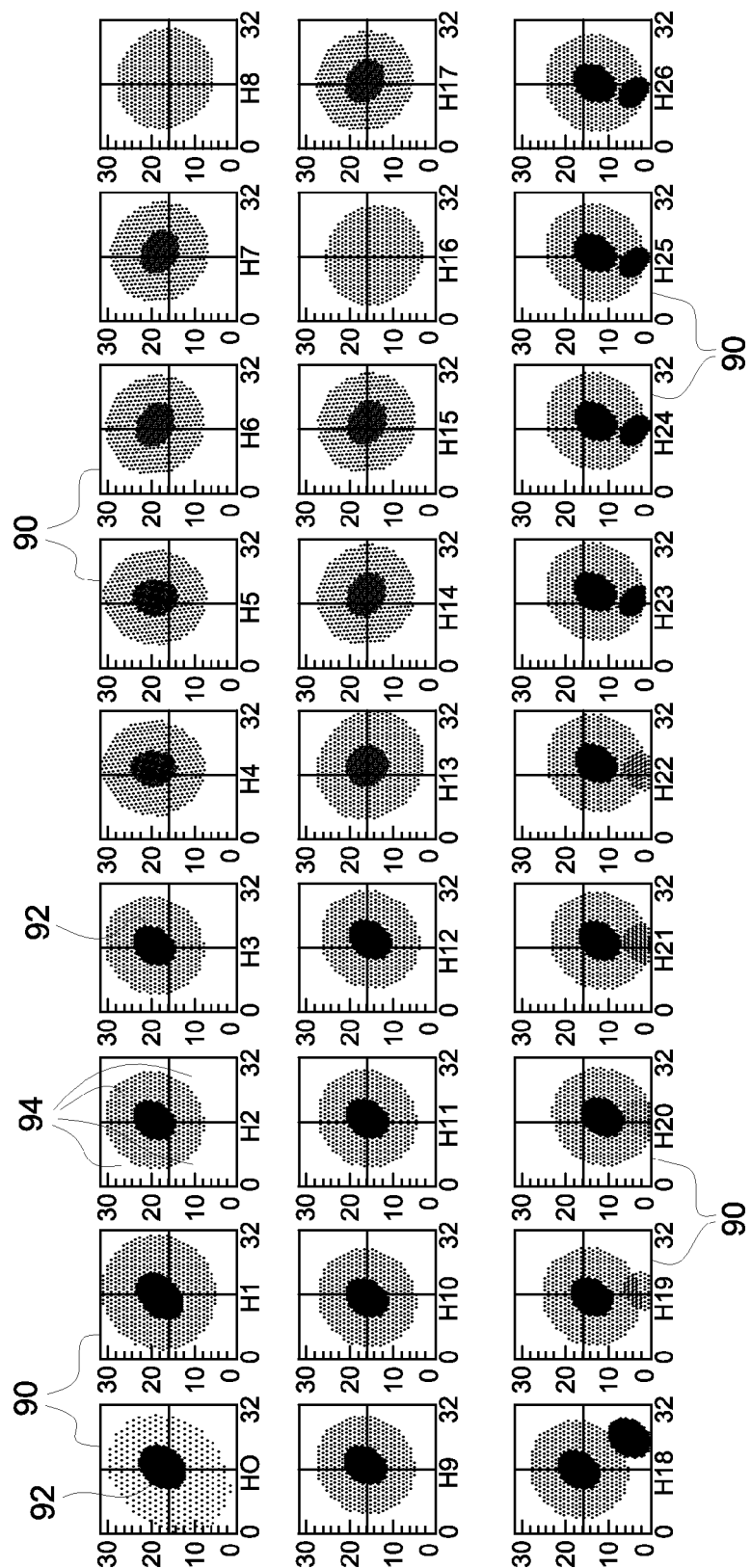
FIG. 5 depicts a sequence of images obtained from an imaging system having four modules per image in accordance with embodiments of the present techniques.

The AED formula described may provide for a reduction in the number of modules of the SPECT system 10 necessary for obtaining images of a region of interest. FIG. 5 depicts a sequence of images 90 obtained from a UFC imaging system. Each image 90 depicts a different view of a region of interest 92, i.e., the left ventricle of the heart. As shown in FIG. 5, each image 90 may be produced by 4 modules (e.g., a camera or detector having one or more modules) such that each module produces a quadrant 94 to compose each image 90. Thus, to produce the sequence of images 90 depicted in FIG. 5, a total of 108 modules are required.

Figure 6:
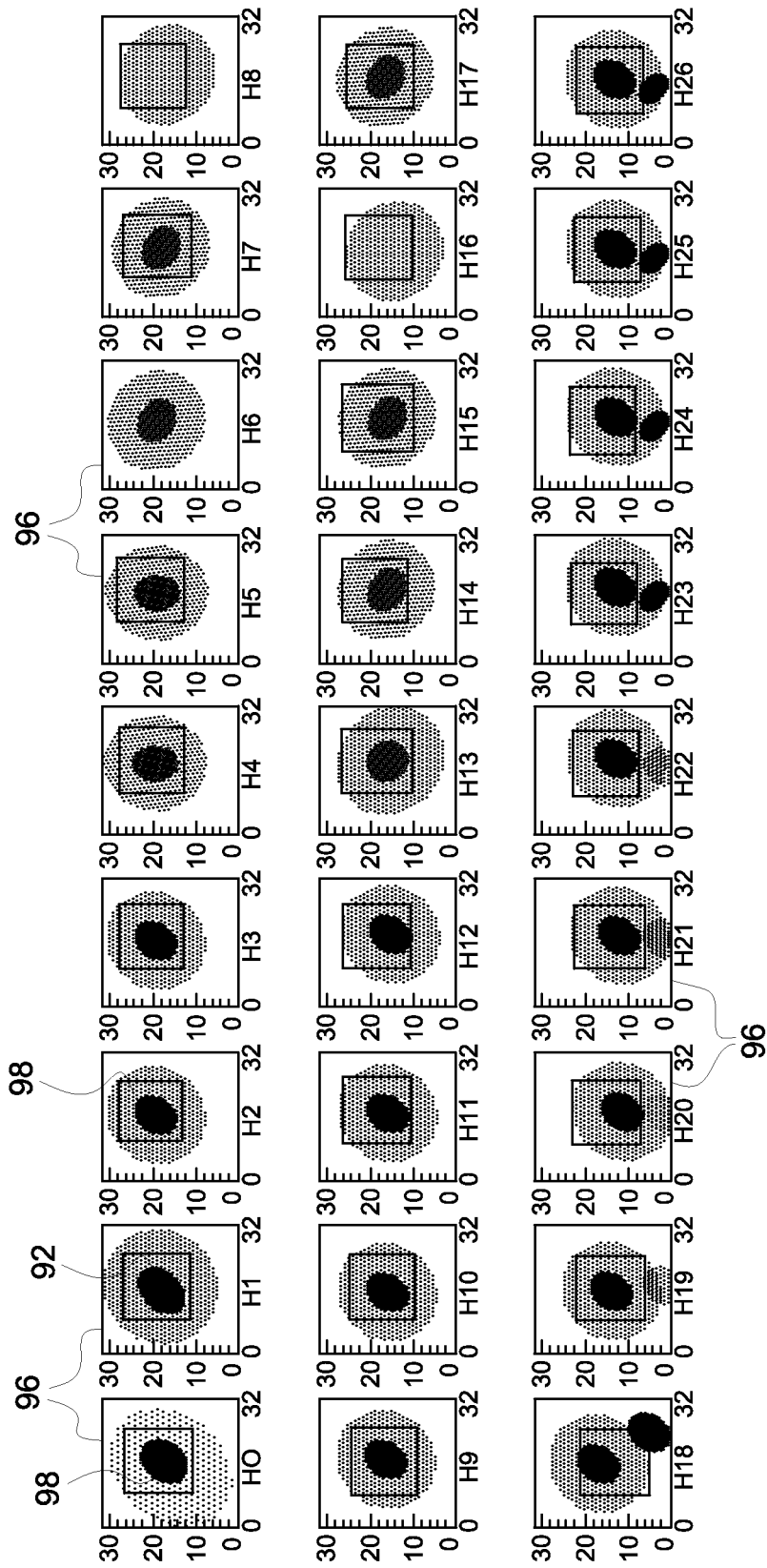
FIG. 6 depicts a set of images obtained from an imaging system having one module per image in accordance with embodiments of the present techniques.

The AED formula discussed above may enable the reduction of modules used for producing images of a region of interest, while increasing focus on the region of interest 92 due to the relative emphasis on the foreground data over the background data. For example, FIG. 6 depicts a sequence of images 96 of the left ventricle of the heart obtained by a UFC imaging system having a reduced number of modules relative to the system of FIG. 5. In contrast to FIG. 5, each image 96 may be produced by a single module using the AED formula described above. As shown in FIG. 6, each image 96 includes a single area 98 depicting the focus of the module that produced the respective image 96. Thus, to produce the sequence of images 96 depicted in FIG. 6, a total of 27 modules may be used. As compared to the images 90 of FIG. 5, the images 96 produced by the AED formula may show an increased focus on the region of interest 92 while maintaining comparable or better image quality than the images 90 produced using 4 modules.

Figure 7:
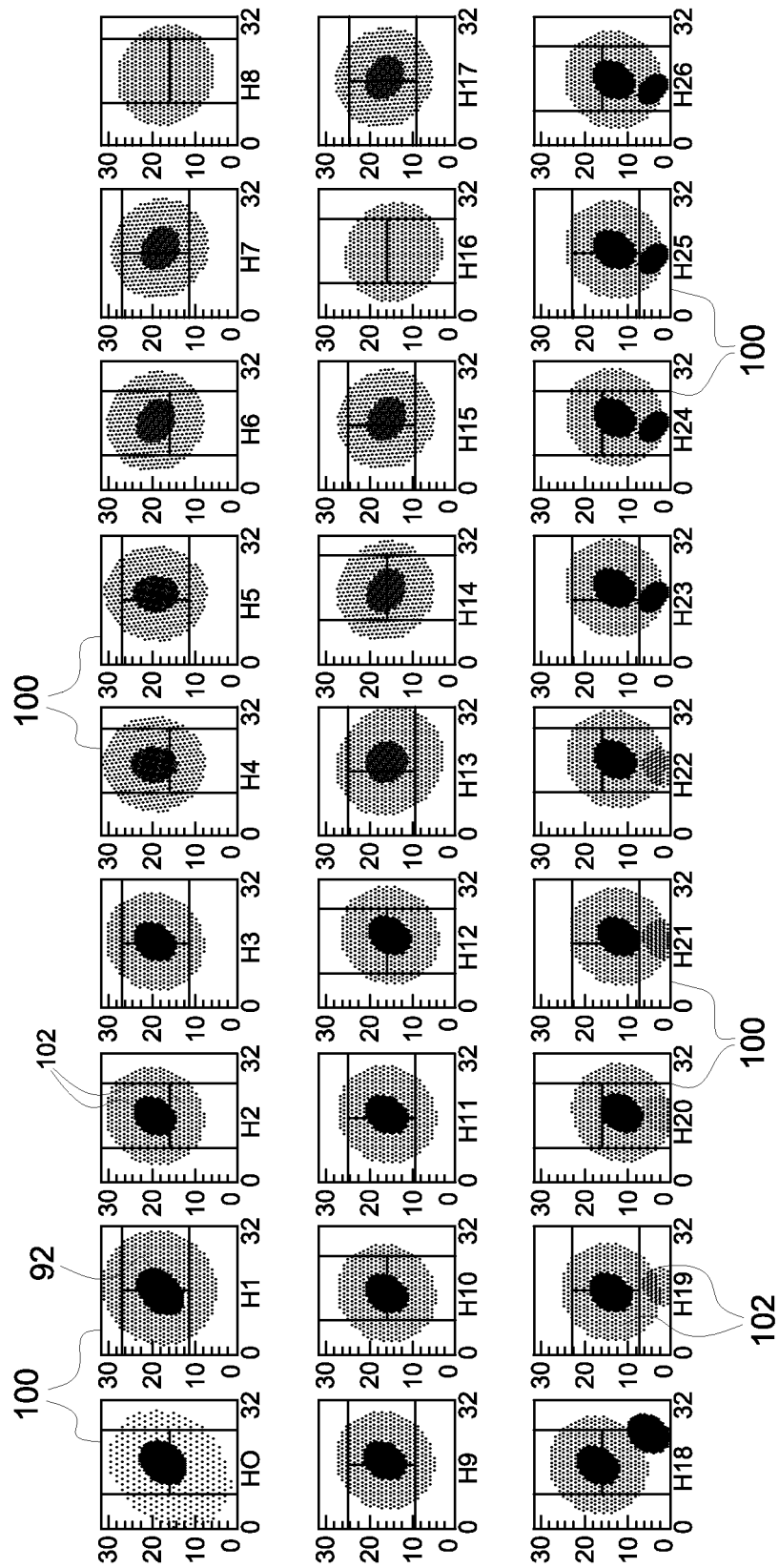
FIG. 7 depicts a set of images obtained from an imaging system having two modules per image in accordance with embodiments of the present techniques.

In other embodiments, the number of modules may be reduced to two modules per image. For example, FIG. 7 depicts a sequence of images 100 of the left ventricle of the heart in which each image is produced by 2 modules using the AED formula described above. As shown in FIG. 7, each image 100 includes 2 areas 102 corresponding to the 2 modules used to produce the image. Thus, to produce the sequence of images 100 depicted in FIG. 7, a total of 54 modules may be used. Again, as compared to the images 100 of FIG. 5, the images 100 produced by the AED formula may show an increased focus on the region of interest 92 while maintaining comparable or better image quality than the images 100 produced using 4 modules per image. In other embodiments, a SPECT imaging system may use a combination of the techniques depicted in FIGS. 6 and 7, such as by using 1 module for some images and 2 modules for other images.

Figure 8:
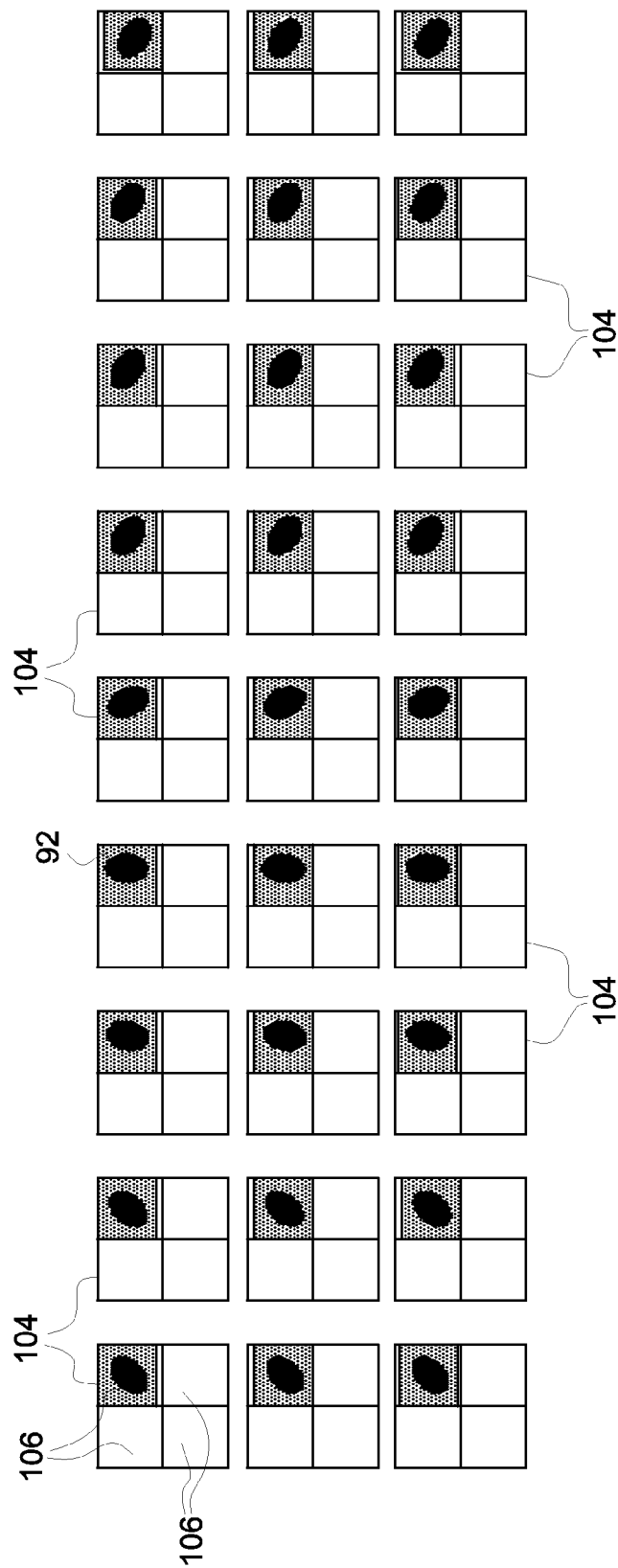
FIG. 8 depicts a set of images obtained from an imaging system having one module per image and a shifting pinhole assembly in accordance with embodiments of the present techniques.

In other embodiments, the AED formula may enable use of additional techniques with the reduced modules described above in FIGS. 6 and 7. FIG. 8 depicts a sequence of images 104 each produced by 1 module using a shifting pinhole for the camera of the module in accordance with one embodiment. As shown in FIG. 8 each image 104 may include four quadrants 106. Each quadrant may be produced by shifting the pinhole of the camera of the module. For example, in one embodiment the pinhole may be shifted by approximately 6 mm. Each shift and subsequent image capture may produce a quadrant 106 of each image. However, as each image is produced by a single module, a total of 27 modules may be used to produce the sequence of images 104 depicted in FIG. 8.

Figure 9:
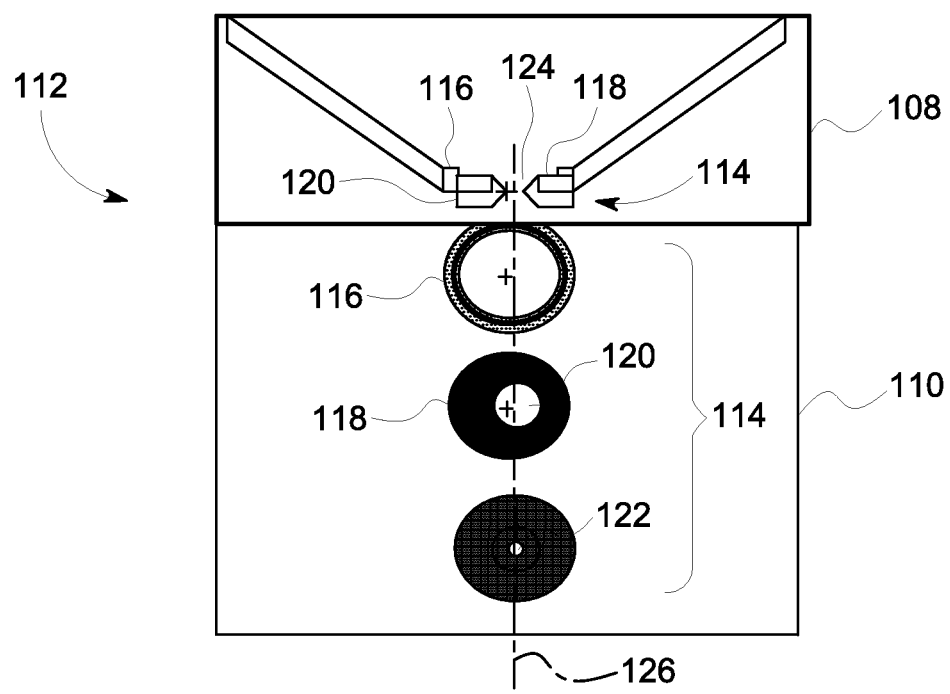
FIG. 9 depicts a cross-section and exploded view of a shifting pinhole assembly such as used in FIG. 8 in accordance with embodiments of the present techniques.

FIG. 9 depicts a cross-section 108 and exploded view 110 of a collimator 112 having a shifting pinhole assembly 114 in accordance with an embodiment of the present techniques. The shifting pinhole assembly 114 may include a ring 116, a washer 118 with an eccentric hole 120, and a pinhole 122 concentrically aligned with an aperture 124 of the collimator 112 around an axis 126. To produce the images 104 described above in FIG. 8, the eccentric hole 120 may be shifted in different directions perpendicular to the axis 126. Each shift may enable production of a different quadrant of each of the images 104, by blocking and exposing the aperture 124 to radiation received through the pinhole 124.

Figure 10:
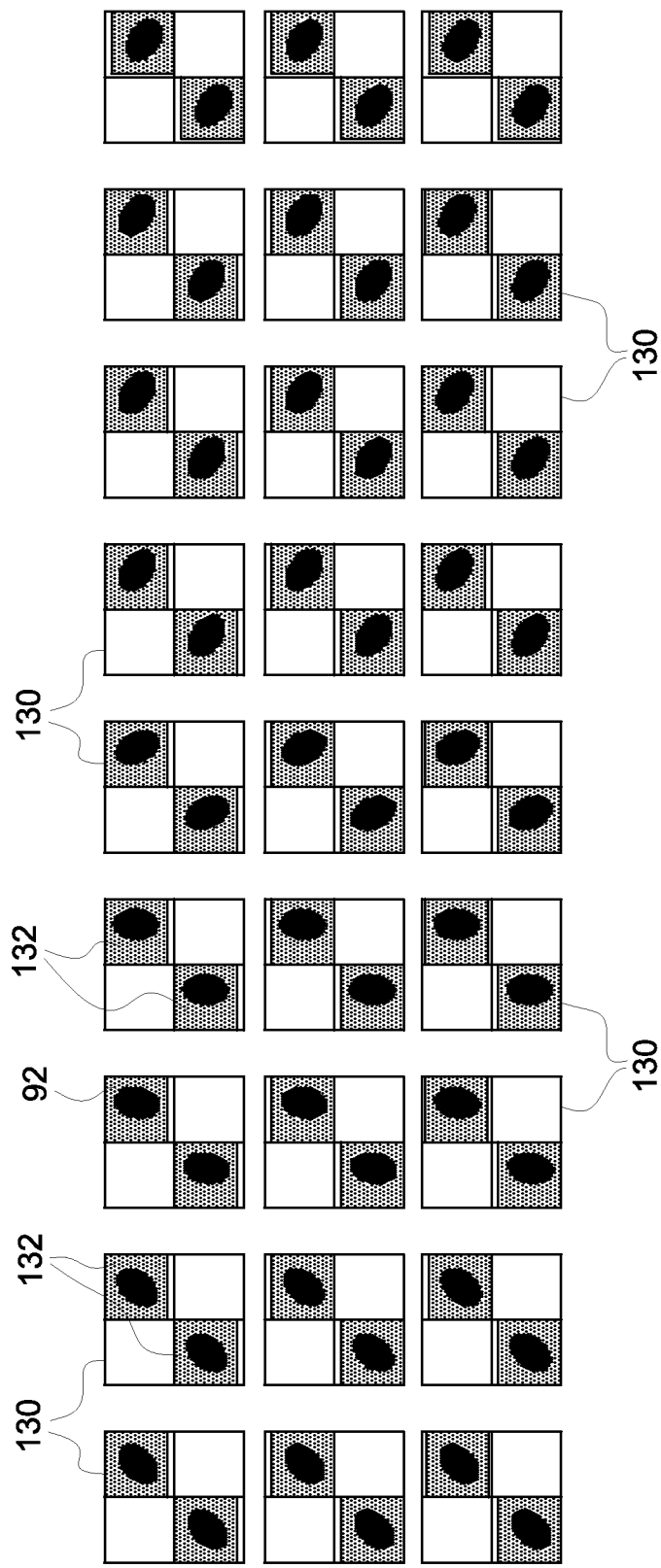
FIG. 10 depicts a set of images obtained from an imaging system having two modules per image and a double pinhole in accordance with embodiments of the present techniques.

In other embodiments, an imaging system may use a camera having double pinholes. FIG. 10 depicts a sequence of images 130 each produced by 2 modules through a double pinhole camera in accordance with an embodiment of the present techniques. As shown in FIG. 10, each image 130 may include two areas 132. Each area 132 may be produced by using one pinhole and camera of one of the 2 modules that produce the image. For example, the area 132A may be produced by one of the 2 modules and the area 132B may be produced by the other one of the 2 modules. However, as each image 130 is produced by 2 modules, a total of 54 modules may be used to produce the sequence of images 130 depicted in FIG. 10, with each image 130 including two views, i.e., areas 132.

Figure 11:
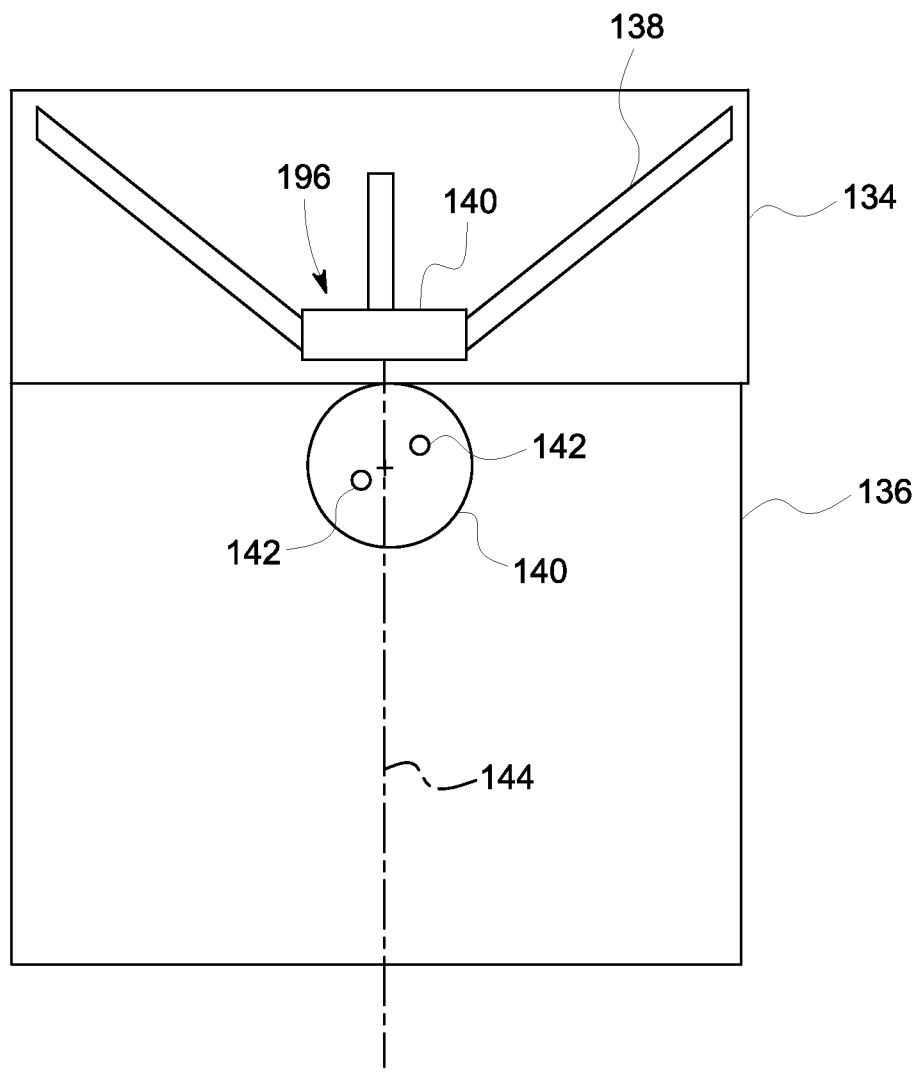
FIG. 11 depicts a cross-section and exploded view of a double pinhole assembly such as used in FIG. 10 in accordance with embodiments of the present techniques.

FIG. 11 depicts a cross-section 134 and exploded view 136 of a collimator 138 having a double pinhole assembly 140 in accordance with an embodiment of the present techniques. The double pinhole assembly 140 may include two pinholes 142 disposed around an axis 144 of an aperture 146 of the collimator 138. To produce the images 130 described above in FIG. 10, the detectors of each of the two modules may capture the areas 132 through a respective pinhole 142.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of reconstructing an image, comprising:
   receiving pixel data from a gamma camera of an imaging system; and
   calculating a voxel value from the pixel data, wherein calculating the voxel value includes at least the acts of:
   subtracting an expected pixel value from a measured pixel value of the pixel data to produce a difference; and
   correcting a previous voxel value by adding a weighted value of the difference to the previous voxel value.

2. The method of claim 1, comprising receiving gamma radiation at the gamma camera from a radiopharmaceutical injected into a subject.

3. The method of claim 2, comprising rotating the gamma camera around the subject.

4. The method of claim 1, comprising collimating gamma radiation during the receiving.

5. The method of claim 1, comprising reconstructing a three-dimensional image from the voxel values.

6. The method of claim 1, comprising receiving pixel values from a second gamma camera of the imaging system.

7. An imaging system, comprising:
   a detector; and
   image processing circuitry coupled to the detector, wherein the image processing circuitry executes code, stored on a non-transitory, tangible machine-readable medium, for reconstructing a three-dimensional image from pixel data received from the detector, wherein the code, when executed, performs the following:

iteratively processes the pixel data to produce voxels of a three-dimensional image, wherein a voxel value $V_j^{(k-1)}$ of an iteration is determined such that:

$$V_j^{(k+1)} = V_j^{(k)} + \frac{1}{\sum m_{ij}^{-1}} \sum (P_i - \langle P_i \rangle) m_{ij}^{-1},$$

and where
k is the iteration;
j is the voxel index
m is the geometrical weight;
P is the measured pixel value;
<P> is the expected/estimated pixel value; and
i is the pixel index.

8. The imaging system of claim 7, wherein the image processing system comprises an operator workstation configured to display the three-dimensional image.

9. The imaging system of claim 7, comprising a shifting pinhole coupled to a collimator of the detector.

10. The imaging system of claim 7, comprising a double pinhole coupled to a collimator of the detector.

11. The imaging system of claim 7, wherein the image processing circuitry reconstructs an image from pixel data received from the detector.

12. The imaging system of claim 7, comprising a second detector, wherein the code, when executed, reconstructs an image from pixel data received from the detector and the second detector.

13. The imaging system of claim 7, wherein the code, when executed, iteratively processes the pixel data until a convergence criterion is met.

14. The imaging system of claim 7, wherein the detector comprises one or more modules.

15. The imaging system of claim 7, wherein the detector comprises a cadmium zinc telluride (CZT) solid-state detector.

16. A method of reconstructing an image, comprising:
detecting gamma radiation at a detector;
iteratively processing pixel data received from the detector on processing circuitry of an image processing system to produce voxels of a three-dimensional image, wherein a voxel $V_j^{(k+1)}$ of an iteration is determined such that:

$$V_j^{(k+1)} = V_j^{(k)} + \frac{1}{\sum m_{ij}^{-1}} \sum (P_i - \langle P_i \rangle) m_{ij}^{-1},$$

and where
k is the iteration;
j is the voxel index
m is the geometrical weight;
P is the measured pixel value;
<P> is the expected/estimated pixel value; and
i is the pixel index.

17. The method of claim 16, comprising receiving gamma radiation at the detector from a radiopharmaceutical injected into a subject.

18. The method of claim 16, comprising rotating the detector around the subject.

19. The method of claim 16, comprising reconstructing a three-dimensional image from the voxel values.

20. The method of claim 16, comprising receiving pixel values from a second detector.

* * * * *